United States Patent [19]
Beck et al.

[11] Patent Number: 5,838,158
[45] Date of Patent: Nov. 17, 1998

[54] MEASURING SYSTEM FOR MEASURING THE AMOUNT OF DIELECTRIC IN A WEB

[75] Inventors: David A. Beck, Appleton, Wis.; Wayne L. Miller, Stanhope, N.J.

[73] Assignee: Appleton Mills, Appleton, Wis.

[21] Appl. No.: 512,716

[22] Filed: Aug. 8, 1995

[51] Int. Cl.$^6$ .................................................. G01N 22/00
[52] U.S. Cl. .......................................... 324/636; 324/634
[58] Field of Search ................................. 324/636, 639, 324/640, 663, 642, 643, 646, 634; 364/550

[56] References Cited

U.S. PATENT DOCUMENTS

| | | | |
|---|---|---|---|
| 3,458,808 | 7/1969 | Agdur | 324/58.5 |
| 4,103,224 | 7/1978 | Taro et al. | 324/58.5 C |
| 4,155,035 | 5/1979 | Fitzky | 324/58.5 C |
| 4,203,067 | 5/1980 | Fitzky et al. | 324/58.5 C |
| 4,211,970 | 7/1980 | Fitzky et al. | 324/58.5 C |
| 4,270,083 | 5/1981 | Fitzky et al. | 324/58.5 C |
| 4,297,874 | 11/1981 | Sasaki | 73/73 |
| 4,381,485 | 4/1983 | Steinbrecher | 324/636 |
| 4,829,233 | 5/1989 | Flemming et al. | 324/58.5 C |
| 4,890,054 | 12/1989 | Maeno et al. | 324/58.5 C |
| 4,904,928 | 2/1990 | Lewis | 324/636 |
| 5,039,947 | 8/1991 | Kraszewski et al. | 324/634 |
| 5,177,444 | 1/1993 | Cutmore | 324/639 |
| 5,731,990 | 3/1998 | Beck | 364/550 |

OTHER PUBLICATIONS

W.J. Chudobiak, IEEE Transactions on Instrumentation & Measurement vol. IM–28, No. 1, Mar. 1979, pp. 18–25.
M. Kent, "Applications of Two–Variable Microwave Techniques . . . " Trans Inst. Mc. vol. 11, No. 2, Apr.–Jun. 1989 pp. 58–62.
E. Stotzer et al, IG ARSS '86 "Dielectric and Surface Parameters Related to Microwave Scatter . . . ", University of Bern, Switzerland Sep. '86.
R.J. King, KDC Technology Corp, "Microwave Sensors for Process Control . . . " Sensors, Sep. 1992 pp. 68–74.
A.W. Kroszewski et al, "Microwave Resonator as a Dielectric Object Sorting Device: . . . " US Dept of Agric., Russel Ag. Research Center, Athens, GA, pp. 435–441, date unknown.
T. Okabe et al "A New Method for the Measurement of Grain Moisture Content by Use of Microwaves", J. Agric. Engng Res, 1973, 18, 59–66 (no month).
C.C. Habeger et al, "The Microwave Dielectric Constants of Water–Paper Mixtures: . . . " Journal of Applied Polymer Science, vol. 28, pp. 969–981, 1983 (no month).

*Primary Examiner*—Christine K. Oda
*Attorney, Agent, or Firm*—Thomas D. Wilhelm

[57] ABSTRACT

An instrument determines one or more physical properties, including dielectric, in a web or other material. A resonant cavity in the instrument resonates at a known band of frequencies. The instrument generates a constant frequency signal within the known band, divides the signal into a measuring signal and a reference signal. With the instrument proximate the web, the measuring signal is passed into the resonant cavity. A first fraction passes through the resonant cavity. incurring a phase shift. A second fraction is reflected from the cavity. The phase shift in the measuring signal is compared to the reference signal, and a first output signal is sent to a controller. The magnitude of the reflected signal is determined, and a second output signal is sent to the controller. Using the first and second output signals, the controller calculates a resultant property value (e.g. moisture content), using the combined values of phase shift and reflected power to cancel out the affect of distance of the e.g. moisture from the resonant cavity. The instrument can also determine length, speed of travel, and temperature of the web, and the controller can combine such measurements mathematically, determining the location in the web of, for example, given readings of moisture and temperature, as well as the general condition of the web.

27 Claims, 3 Drawing Sheets

5,838,158

MEASURING SYSTEM FOR MEASURING THE AMOUNT OF DIELECTRIC IN A WEB

FIELD OF THE INVENTION

This invention relates to instruments and methods for measuring moisture and other properties extant in a material or web, e.g. a travelling web.

BACKGROUND OF THE INVENTION

This invention pertains to the measurement of moisture and other relevant properties extant in a material or web, including, but not limited to, properties of speed, length, temperature, and vibration.

Hereinafter, the invention is described with respect to its application to the detection of moisture and other properties extant in a papermaking felt. It is contemplated that both the instruments of the invention and the methods of the invention have application to a variety of situations and materials requiring a non-destructive method of determining moisture content and/or other properties in respective materials. While the description concentrates on a travelling closed-loop web, e.g. a papermaking felt, it is appreciated that similar applications can be made for other uses, and in other industries, in light of the description of the invention herein.

In the papermaking industry, it is desirable to periodically determine the condition of a papermaking felt used in the papermaking process, so as to adjust the operation of the felt or to anticipate, and plan for, replacing the felt. Determining the moisture content of the felt is useful for determining the effectiveness of operation of the papermaking machine, and also the condition of the papermaking felt. It is also desirable to measure other properties pertaining to the felt, including speed and length. As a felt wears it changes size. Hence, periodically measuring the length of a felt provides information useful for determining the need to replace, or more closely monitor, a particular felt.

It is also desirable to measure the temperature of the felt at various positions across its width and along its length. In addition to moisture content, temperature variations may also indicate equipment problems or the condition of the felt.

The collection of vibration data is useful for determining if vibrations within the papermaking machine can be correlated to moisture or other properties in the felt.

Yet another desirable capability for test instruments used in conjunction with papermaking lies in correlating moisture, temperature, and vibration data to specific locations on a particular papermaking felt. Collecting and storing such data concurrently with speed and length measurements can provide resultant data useful for making such correlations.

It is also desirable to compare moisture, temperature, and/or vibration data for a given location on the felt to manufacturing data for the specific felt to identify possible anomalies in materials used, or manufacturing practices.

It is desirable for an instrument used to measure moisture and other properties in a material or web to be capable of taking a series of readings closely spaced in time, each reading giving a measure of the property of interest.

Where a series of readings for a particular property is taken across the width of a papermaking felt of other web, the repeat rate of the instrument as to that property determines the spacing across the width of the web represented by consecutive readings. The repeat rate for the several property measurements differs according to the specifics for the respective sensors and electric circuitry.

It is desirable to standardize the number of data points with respect to the length of the path along which the data points were collected, for example along the length of the web, such that each data point represents a fixed, uniformly repeated portion of the length of the path. The path may, of course, extend across the width of a stationary or moving e.g. closed loop web. Such standardizing allows historical data on a particular felt to be easily compared with a present reading to help identify ongoing changes in the condition of the felt over its use life, and changes in the environment in which the felt is operating.

It is an object of this invention to provide methods for determining the moisture in a web or other material.

It is another object to provide methods for determining the condition of a web through measurement of relevant properties including, but not limited to, moisture, speed, length, temperature, and vibration.

It is a further object of this invention to provide a method for correlating moisture, temperature, and/or vibration data to particular loci on the web.

It is yet another object of this invention to provide methods for obtaining a fixed number of data points independent of the repeat rate or measurement time for a given property measurement.

It is yet a further object of this invention to provide an instrument for measuring moisture in a material or web.

It is still another object of this invention to provide a resonant cavity for transmitting a microwave signal into the material in which a property is to be measured.

SUMMARY OF THE DISCLOSURE

The invention comprehends novel instruments and methods, for collecting data and thereby determining the amount of dielectric, including moisture, in a material, along with other physical properties, including storing dielectric (e.g. moisture) and other properties concurrently, and mathematically manipulating the data in arriving at the determinations. The summary and description hereafter refer to a travelling web as the preferred material from which data is collected. The possible uses of the invention are not, however, limited to travelling webs. The invention also applies to static webs, and other non-web materials. A preferred application of the instrument is to determine moisture, and indirectly conditions of manufacture and use, of a papermaking felt.

A first family of embodiments comprises a measuring system for measuring the amount of dielectric in a web. The measuring system includes a measuring instrument having an electric circuit, the electric circuit comprising an electric energy source, for emitting a constant frequency signal; a power divider for dividing the constant frequency signal into a reference signal at a reference terminal, for travelling along a reference path, and a measuring signal at a measuring terminal, for travelling along a measurement path; a receptacle comprising a resonant cavity having at least one resonant frequency, the receptacle being electrically connected to the electric energy source such that a first traversing fraction of the measuring signal, corresponding to the at least one resonant frequency, traverses along the measurement path, through the resonant cavity, and wherein a second fraction of the measuring signal is reflected from the resonant cavity, the receptacle being positioned in the measuring instrument to accommodate placing the resonant cavity proximate the web, the resonant cavity being adapted to cause a phase shift in the traversing fraction in response to the dielectric in the web, such that the phase of the traversing fraction is shifted relative to the phase of the reference signal, the magnitude of the phase shift in the traversing fraction being a function of the amount of dielectric in the web; a phase difference detector for receiving the reference signal and the first portion of the measuring signal after the traversing fraction traverses the resonant cavity, the phase difference detector being adapted to detect the difference between the phase of the reference signal and the phase of the traversing fraction and to provide a first output signal, the magnitude of the first output signal depending on the magnitude of the difference in phase so detected, the first output signal providing a first representation of the amount of dielectric in the web; and a reflected power detector electrically connected between the receptacle and the measuring terminal of the power divider, for providing a second output signal, the magnitude of the second output signal depending on the magnitude of the reflected second fraction of the measuring signal, the second output signal thus comprising a second representation of the amount of dielectric in the web.

In preferred embodiments, the invention comprehends including a controller adapted to compare the first and second output signals to data stored in the controller, thereby to cancel out the affect of the distance between the resonant cavity and the dielectric (e.g. moisture) being detected, and to generate a third output signal, the third output signal being a more nearly accurate representation of the dielectric in the web than either of the first and second output signals.

In general, the difference in phase, as detected in the phase difference detector, is a function of dielectric properties in the web.

Preferably, the electric energy source comprises, in combination, a varactor-tuned oscillator having a third output signal, a single-frequency crystal oscillator having a fourth output signal, and a phase-locking circuit comprising the varactor-tuned oscillator and the single-frequency crystal oscillator, a portion of the third output signal being routed through the phase locking circuit, the phase locking circuit being configured to synchronize the varactor tuned oscillator with the single-frequency crystal oscillator to thereby stabilize the frequency of the third output signal.

In preferred embodiments, the receptacle comprises a tuned transmission line in the resonant cavity, preferably first and second transmission rods, and a variable matching device for altering the reactive impedance of the resonant cavity. The transmission line typically has input and output terminals, the variable matching device comprising a varactor diode electrically connected to at least one of the first and second transmission rods at the input terminal.

The receptacle preferably has a plurality of walls, and an open top, including a top surface, the measuring instrument comprising a top wall, e.g. of acrylonitrile butadiene styrene copolymer, propinquant the top surface, the top wall being adapted to transmit microwave energy from the resonant cavity into e.g. a papermaking felt with negligible attenuation, a known fixed amount of change in phase, and negligible change in frequency.

The transmission line is preferably constructed of a material having a coefficient of thermal expansion no greater than $4 \times 10^{-6}$ inch per inch length degree Celsius at room temperature. A typical such material comprises about 60 to about 65 percent by weight iron, about 34 to about 39 percent by weight nickel, and about 0.5 to about 1.5 percent by weight manganese.

An exemplary phase difference detector comprises a phase locked loop, including a variable phase shifter having a third output signal; a phase detector having a fourth output signal, and having as inputs, the third output signal of the phase shifter, and the first traversing fraction of the measuring signal as modified by passage through the resonant cavity; and an integrator having, as an input, the fourth output signal of the phase detector, the integrator providing a fifth output signal, including a control signal to the variable phase shifter for forcing the reference signal and the first traversing fraction to arrive at the phase detector in quadrature, and thereby forcing the output signal of the phase detector to a null, the output signal of the integrator, after achieving the null, being representative of the phase difference between the reference signal and the first traversing fraction of the measuring signal.

The electric circuit may include a bias tee electrically connected between the measuring terminal of the power divider and the resonant cavity, for providing a bias on the variable matching device, to thereby control the sensitivity, of the tuned transmission line, to the amount of dielectric in the web, and to control the ratio between the amounts of reflected power versus traversing power.

The measuring system may further include, in the measuring instrument, first and second switching devices electrically connected to the input and output terminals, respectively, of the resonant cavity, a first position of the switching devices directing the measuring signal to the resonant cavity, a second position of the switching devices directing the measuring signal to bypass the resonant cavity and pass along an alternate signal path, which can provide a phase shift standard, independent of dielectric adjacent the resonant cavity, whereby the first output signal of the phase difference detector correlates with phase shift caused by circuit elements within the measuring system. Preferably, the alternate signal path comprises a signal conductor of known phase length and know mismatch.

A variable phase shifter, having a variable control input signal, for varying the phase length of the measurement path, may be connected in series with the measuring terminal of the power divider, and when the first and second switching devices are positioned to bypass the resonant cavity, the phase shifter control input can be varied to change the phase length of the measurement path, thereby compensating for circuit errors and restoring a known calibration condition prior to taking measurements.

The measuring system may include a temperature measuring device, preferably an infrared detector, for measuring temperature in the web, and means to compensate the first output signal for temperature variations.

The electric circuit preferably includes at least one attenuation device and at least one signal amplification device in series with each of the measurement path and the reference path, the at least one attenuation device in each path being effective to attenuate power reflected back through the respective circuit elements toward the power divider, the at least one signal amplification device in each path being effective to maintain amplitudes in the respective signals sufficient for detecting the phase difference between the reference signal and the measuring signal in the phase difference detector.

Preferably, the reflected power detector comprises a reflected power bridge having an output signal, and a radio frequency detector electrically connected to the reflected power bridge, to measure the magnitude of the output signal from the reflected power bridge, and to provide an output signal dependent on the magnitude of the output signal from the reflected power bridge.

In a second family of embodiments, the invention comprehends a measuring system for measuring the amount of dielectric in a web. The measuring system includes a measuring instrument having an electric circuit, the electric circuit comprising an electric energy source, for emitting a constant frequency signal; a reflection device electrically connected to the electric energy source, for reflecting a fraction of the signal back through the electric circuit; and a reflected power detector electrically connected in the electric circuit between the reflection device and the electric energy source, for providing an output signal, the magnitude of the output signal depending on the magnitude of the reflected fraction of the constant frequency signal, the output signal comprising a representation of the amount of dielectric in the web.

In a third family of embodiments, the invention comprehends a measuring system for measuring the amount of dielectric in a closed loop web having a length and a width, and traveling at a speed, the measuring system comprising a measuring instrument including (i) a dielectric detector for collecting dielectric readings comprising a first set of data relating to dielectric in the closed loop web and generating a dielectric signal, and (ii) at least one sensor positioned in said measuring instrument to sense an intermittently occurring property extant in a mark extending across the width of the web, thereby to collect a second set of data useful for determining the length of the closed loop web; and a data storage device, for storing the second set of data concurrently with the first set of data, thus to provide a first composite set of data, comprising the first and second sets, useful for determining physical locations on the web represented by respective ones of the dielectric readings in the first set.

The measuring system preferably includes a controller adapted to manipulate the first and second sets of data, thereby to determine physical locations on the web represented by ones of the dielectric readings in the first set.

The measuring instrument preferably includes a temperature measuring device, preferably an infrared sensor, for collecting a third set of temperature data, the data storage device being adapted to receive and store the first and second sets of data concurrently with the third set, thus to provide a second composite set of data, comprising the second and third data sets, representing the physical location on the web represented by respective ones of the temperature readings in the third set.

The measuring system may include a vibration sensor, for collecting a fourth set of data relating to vibration in equipment conveying and/or operating on the web, the data storage device being adapted to receive and store the vibration data concurrently with the dielectric, speed, and length, and optionally temperature, data, thus to provide a composite set of data, representing the physical location on the web represented by ones of the readings of the vibration data.

In a fourth family of embodiments, the invention comprehends a receptacle assembly for use in an electronic measuring instrument, the receptacle assembly comprising a receptacle having a plurality of walls and an open top, including a top surface. The plurality of walls and the top surface, in combination, define an open-top resonant cavity. The receptacle further includes a tuned transmission line in the resonant cavity, the tuned transmission line being oriented in a plane parallel to the top surface, the transmission line being constructed of material having a coefficient of thermal expansion no greater than $4\times10^{-6}$ inch per inch length degree Celsius at room temperature.

The tuned transmission line preferably comprises first and second transmission rods, having input and output terminals, and a variable matching device comprising a varactor diode electrically connected to at least one of the first and second transmission rods at the input terminal, for altering the reactive impedance of the resonant cavity. Preferably, the material comprising the transmission line is about 60 to about 65 percent by weight iron, about 34 to about 39 percent by weight nickel, and about 0.5 to about 1.5 percent by weight manganese.

Preferably, the receptacle assembly includes a bias tee, electrically connected to the receptacle, for imposing a bias on the variable matching device, to thereby control the sensitivity of the tuned transmission line.

The receptacle assembly may include first and second switching devices electrically connected to the input and output terminals respectively of the resonant cavity, a first position of the switching devices directing a signal to pass into the resonant cavity, a second position of the switching devices directing a signal to bypass the resonant cavity and pass along an alternate signal path, preferably a coaxial signal conductor of known phase length, the alternate signal path thus providing a phase shift independent of the resonant cavity.

In a fifth family of embodiments, the invention comprehends a method of collecting data including an unspecified number of data values, and providing a fixed number of data points therefrom. The method comprises the steps of collecting data values at a given uniform repeat rate of preferably at least about 500 readings per second, along a path, the path having a length; storing a first set of successive ones of the data values so collected in a first memory device, as data points, the first memory device having a first capacity to store data points in a first fixed number of data receiving elements corresponding to the number of data points in the first set; after storing the first set of data points in the first memory device, collecting and storing successive data values as a second set in a second memory device, as data points, the second memory device having a second capacity to store data points in a second fixed number of data receiving elements; and after storing a number of successive data points of the second set in the second memory device, dithering the first and second sets of data points into the first memory device while maintaining the sequence in which the data values were collected, thereby arriving at a resultant third set of calculated data points in the first memory device, and storing the third set of data points in the first memory device, the number of data points in the third set being equal to the first fixed number of data elements.

In some embodiments in this family, the method comprises, prior to storing the recited second set of data points in the second memory device, storing, in the second memory device, as the second set of data points, a number of the data values sufficient to fill the second memory device; and dithering the first and second sets of data points into the first memory device while maintaining the sequence in which the data values were collected, thereby arriving at a resultant dithered set of calculated data points in the first memory device, and storing the resulting dithered set of data points in the first memory device, the number of data points in the dithered set of data points being equal to the first fixed number of data elements.

In those embodiments where the number of data points in each of the first and second data sets are equal, the method preferably includes the step, after storing the second set of data points in the second memory device, of averaging each successive two data points in the combination of the first and second memory devices, to thereby obtain a third set of data points having resultant average values, and storing the third set of data points in corresponding data elements of the first memory device.

The method may include the step of averaging a number of successive data values equal to the number of data values previously averaged and stored in ones of the data elements of the first memory device, to obtain a data point having a respective average value, and so averaging successive data values, to thereby obtain a fourth set of data points having respective resultant average values, and storing the fourth set of data points in corresponding data elements of the second memory device and, after filling the second memory device, repeating the above steps until the step of collecting data values is terminated, and then, after the step of collecting data values is terminated, dithering the remaining data points, as extant in the second memory device, into the first memory device, thereby arriving at a composite data set in the first memory device, and storing the composite data set in the first memory device such that the data in the first memory device maintains the sequence in which the data values were collected, the number of data points in the composite data set being equal to the first fixed number of data elements.

In a sixth family of embodiments, the invention comprehends a method of collecting data along a path, and identifying discrete fractions of the data so collected to discrete fractions of the path. The method comprises the steps of collecting data values at a given uniform repeat rate along the path, including sensing data values representing a periodically repeating reference element; storing a first set of successive ones of the data values so collected in a first memory device, as data points, the first memory device having a first capacity to store data points in a first fixed number of data receiving elements corresponding to the number of data points in the first set; after storing the first set of data points in the first memory device, collecting and storing successive data values as a second set in a second memory device, as data points, the second memory device having a second capacity to store data points in a second fixed number of data receiving elements; after storing a number of successive data points of the second set in the second memory device, dithering the first and second sets of data points into the first memory device while maintaining the sequence in which the data values were collected, thereby arriving at a resultant third set of calculated data points in the first memory device, and storing the third set of data points in the first memory device, the number of data points in the third set being equal to the first fixed number of data elements, the data values representing the reference element thus separating the data points in the third data set into data subsets; and, with the data so separated into subsets, correlating at least one of the data points in a given subset to a specific fraction of the path, the fraction having a length comprising, as a fraction of the length of the path, a numerator corresponding to the number of data points in the given subset which are being correlated, and a denominator equal to the number of data points in the given subset.

In a seventh family of embodiments, the invention comprehends a method of measuring the amount of moisture in a web. The method comprises the steps of generating an electric signal having a constant frequency; dividing the electric signal into a reference signal and a measuring signal; passing the measuring signal into a receptacle comprising a resonant cavity, the resonant cavity being proximate the web, a first traversing fraction of the measuring signal traversing the resonant cavity, a second reflected fraction of the measuring signal being reflected from the resonant cavity, moisture in the web causing a phase shift in the traversing fraction, the magnitude of the phase shift being a function of the amount of moisture in the web, the magnitude of the reflected fraction being a function of the amount of moisture in the web; detecting, in a phase difference detector, the difference in phase between the reference signal and the traversing fraction; providing a first output signal from the phase difference detector, the magnitude of the first output signal depending on the magnitude of the difference in phase so detected between the reference signal and the traversing fraction, the first output signal providing a first representation of the amount of moisture in the web; measuring, in a reflected power detector, the magnitude of the reflected fraction of the measuring signal; and providing a second output signal from the reflected power detector, the magnitude of the second output signal depending on the magnitude of the reflected fraction of the measuring signal, the second output signal comprising a second representation of the amount of moisture in the web.

The method preferably includes measuring the temperature of the web, and compensating the first and second output signals for temperature variation from a standard, and comparing the first and second output signals to data indicating the affect of distance on the amount of the phase shift and the amplitude of the reflected fraction, and mathematically cancelling out the affect, on the first and second output signals, of distance between the resonant cavity and the moisture in the web.

In an eighth family of embodiments, the invention comprehends a method of measuring the amount of moisture in a web, using an electrical instrument. The method comprises the steps of generating an electric signal having a constant frequency; dividing the electric signal into a reference signal and a measuring signal; positioning, propinquant the web, an electrical reflection device adapted to reflect an electric signal back through the electric circuit, wherein the magnitude of the reflected signal depends on the amount of moisture in the web, and inputting the measuring signal to the reflection device, a fraction of the measuring signal being reflected back from the reflection device; receiving, in a radio frequency detector, the reflected fraction of the measuring signal, and measuring the magnitude of the reflected fraction so received; and providing an output signal from the radio frequency detector, the magnitude of the output signal depending on the magnitude of the reflected fraction, the output signal from the radio frequency detector being a representation of the amount of moisture in the web.

The method preferably includes measuring the temperature of the web, and compensating the output signal for temperature variation from a standard.

In a ninth family of embodiments, the invention comprehends a method for determining the condition of a closed loop web, the web having a length and a width, and travelling at a speed. The method comprises the steps of collecting a first set of data values relating to moisture content in the closed loop web; sequentially sensing an intermittently occurring property extant in a mark extending across the width of the web, thereby collecting second and third sets of data useful for determining the speed and length of the closed loop web; and storing the second and third sets of data concurrently with the first set, thus providing a composite set of data, comprising the first, second, and third sets, useful for determining the physical location on the web represented by ones of the moisture readings in the first set.

The method preferably includes repeatedly sensing the temperature of the closed loop web and thereby collecting a fourth set of temperature data, and storing the second and third sets of data concurrently with the fourth set, providing a second composite set of data, comprising the second, third and fourth sets, for representing the physical location on the web represented by ones of the points of data in the fourth set.

The invention may include collecting a set of vibration data useful for determining the relationship between the closed loop web and equipment conveying and/or operating on the web, and storing the first and second sets of data concurrently with the vibration data, and preferably includes computing a moisture frequency spectrum from the moisture data, computing a vibration frequency spectrum from the vibration data, comparing the moisture and vibration frequency spectra to detect similarities indicating that vibration could be related to moisture in the web, and using the comparison of the moisture and vibration frequency spectra, in combination with the speed and length data, to relate the moisture data to a physical location in the web, hence identifying a locus, in the closed loop web, representing a potential source of vibration, and comparing the locus of potential vibration to manufacturing data for the specific web, to assist in identifying anomalies in materials, or manufacturing practices.

Figure 1:
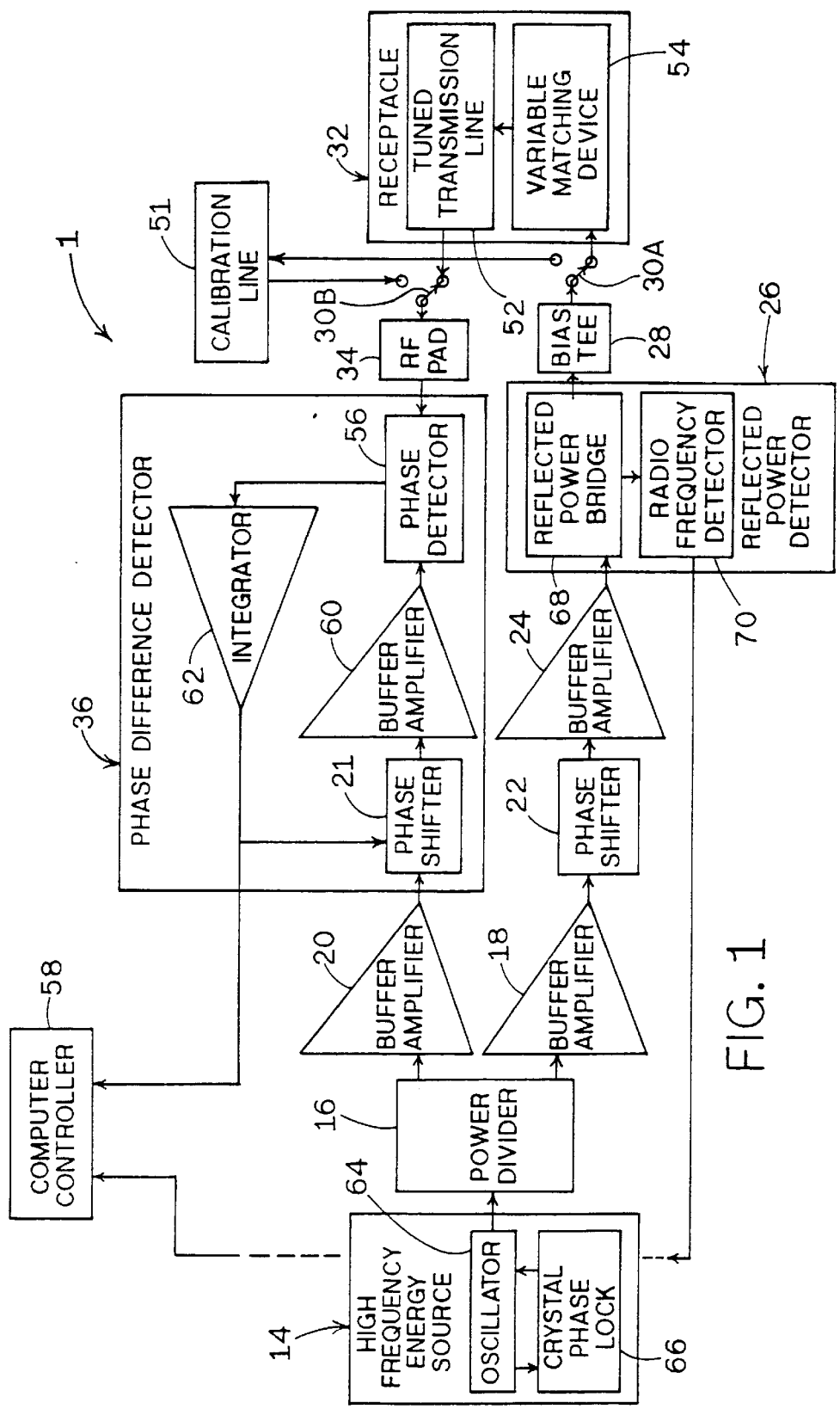
FIG. 1 shows a representative schematic circuit diagram of circuitry used in a measuring instrument of the invention.

It is to be understood that the invention is not limited in its application to the details of construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

Figure 3:
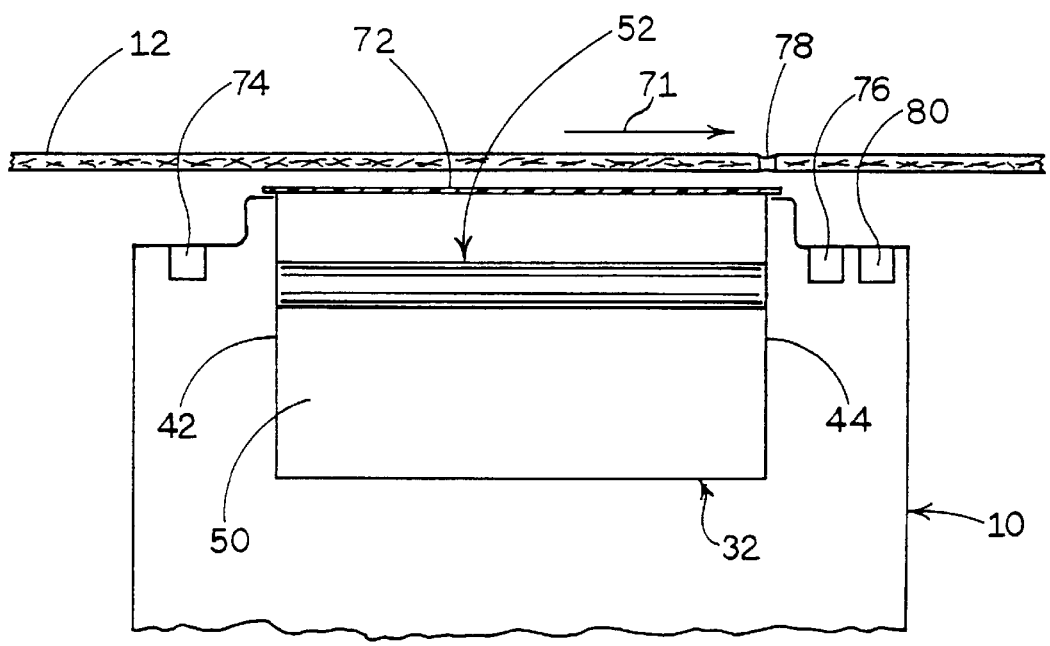
FIG. 3 shows a side elevation, with parts cut away, of a portion of an instrument of the invention.

Referring now by characters of reference to the drawings, FIG. 1 shows an electric circuit 1, for use in an instrument 10 of the invention, to determine moisture and other properties in a web 12, shown in FIG. 3. Referring again to FIG. 1, a high frequency electric energy source 14 provides a constant frequency (e.g. microwave frequency) signal to a power divider 16. The power divider 16 divides the signal from the energy source 14 into a measuring signal and a reference signal, both outputted from power divider 16 at respective measuring and reference terminals (not shown). The measuring signal is passed, through buffer amplifier 18, to variable phase shifter 22. The reference signal is passed, through buffer amplifier 20, to variable phase shifter 21. Buffer amplifiers 18, 20 provide RF isolation within the circuit 1, and amplify the respective reference and measuring signals. The arrowheads in the line circuit diagram of FIG. 1 indicate the general direction of flow of power through the circuit.

Variable phase shifter 22 is electrically connected, through buffer amplifier 24, to reflected power detector 26.

The function of buffer amplifier 24 is similar to that of buffer amplifiers 18, 20, previously described. Reflected power detector 26 is electrically connected to bias tee 28. The bias tee is electrically connected to a receptacle 32 (See FIGS. 2 and 3) through switch 30A. Receptacle 32 is electrically connected through switch 30B to RF pad 34, and from RF pad 34 to phase difference detector 36. Switches 30A and 30B are shown in the default switch position in FIG. 1, wherein a signal is passed through the receptacle 32 to sense e.g. moisture. In the alternate positions of switches 30A, 30B not shown, the measuring signal passes through a calibration line 51 of stable, and known, phase length. Calibration line 51 may be e.g. a coaxial cable of known phase length, relative to the frequency of the signal outputted from energy source 14.

Figure 2:
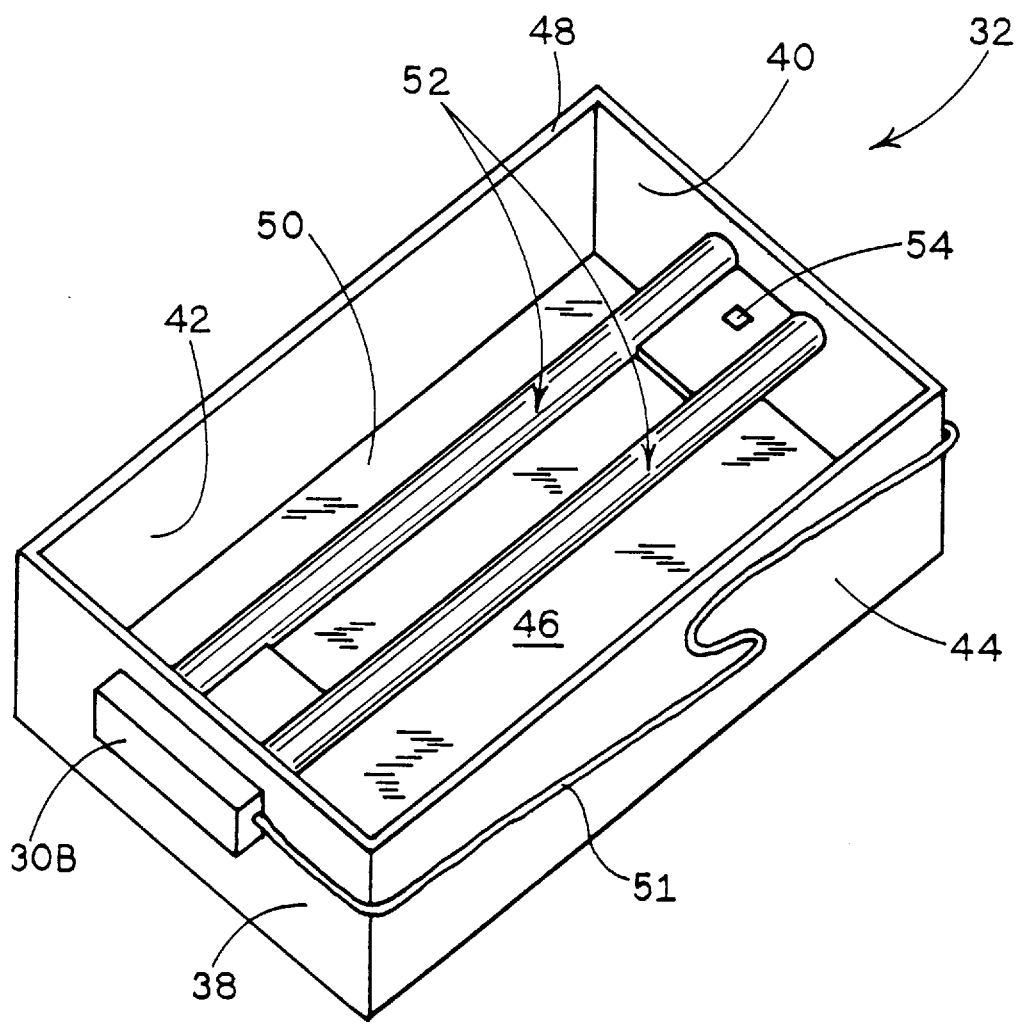
FIG. 2 shows a pictorial view of a receptacle used in an instrument of the invention.

Referring now to FIG. 2, receptacle 32 includes two end walls 38, 40, two side walls 42, 44, a bottom wall 46, a top surface 48, an open top, and a resonant cavity 50 defined between the end walls, side walls, bottom wall, and the open top. Parallel tuned transmission rods 52 traverse the length of the receptacle 32, in the resonant cavity 50, between end walls 38 and 40. A varactor diode 54 is mounted to receptacle 32, in cavity 50, adjacent end wall 40, and is electrically connected in series to one of the tuned transmission rods 52 adjacent end wall 38.

With switches 30A, 30B aligned in the default position as shown, the measuring signal passes from bias tee 28, through switch 30A, into the resonant cavity. A first traversing fraction of the measuring signal traverses through the resonant cavity by way of transmission rods 52, through switch 30B, to RF pad 34. RF pad 34 functions to attenuate the measuring signal and thereby to reduce the amount of reflected power reaching the surrounding circuit elements.

A second reflected fraction of the measuring signal is reflected from the resonant cavity back through bias tee 28 to the reflected power detector 26.

Moisture present in the web 12 causes a phase shift in the traversing fraction of the measuring signal, the amount of the phase shift being a function of the amount of moisture in the web. The amount of moisture in web 12 also affects the magnitude of the reflected fraction of the measuring signal.

The varactor diode 54 receives its input signal from bias tee 28, through switch 30A, and supplies its output signal to the tuned transmission rods 52, thereby operating as a variable impedance matching device. Varying the bias on the variable matching device 54 through bias tee 28 affects the impedance mismatch in the cavity. The impedance mismatch controls the ratio of the amount of power transmitted through the resonant cavity 50 to the amount of power reflected from the cavity, and in addition, controls the amount of phase shift resulting from moisture in the web.

The output signal of the RF pad 34 passes into phase difference detector 36 at phase detector 56. Phase difference detector 36 has, as inputs, the traversing fraction of the measuring signal as outputted from RF pad 34, and the reference signal as outputted from buffer amplifier 20. Phase difference detector 36 measures the difference in phase between the reference signal, as outputted from buffer amplifier 20, and the traversing fraction of the measuring signal as outputted from RF pad 34, and provides, as an output signal, a first property signal giving a first representation of the amount of moisture in the web.

The reflected power detector 26 measures the magnitude of the reflected second fraction of the measuring signal and provides, as an output signal, a second property signal, independent of the first property signal outputted from phase difference detector 36, giving a second representation of the amount of moisture in the web. Thus, the phase difference detector 36 and the reflected power detector 26 give first and second different, and independent representations of the amount of moisture in web 12.

The outputs of the phase difference detector 36 and the reflected power detector are inputted to the computer controller 58. The computer controller has stored, in its memory, a first equation defining the relationship between the output of the phase difference detector and the moisture in the web, and a second equation defining the relationship between the output of the reflected power detector and the moisture in the web. However, neither equation, used alone, accounts for the affect of distance between the resonant cavity and the moisture being detected. Using the inputs from the phase difference detector and the reflected power detector, the computer controller simultaneously solves the two equations, which have two unknowns, to arrive at a more precise calculated representation of the amount of moisture in the web. This effectively cancels out the affect of distance between the cavity and the moisture in the web, thus giving a more precise indication of the actual amount of moisture than either of the signals, outputted from the phase difference detector and the reflected power detector, alone.

The phase difference detector 36 comprises a phase-locked loop including the variable phase shifter 21, buffer amplifier 60, phase detector 56, and integrator 62. The phase detector 56 receives, as inputs, the output of buffer amplifier 60, representing the reference signal, and the output from RF pad 34, representing the traversing fraction of the measuring signal. The output of phase detector 56, representing the phase difference between the reference signal, and the traversing fraction of the measuring signal, is inputted to the integrator 62. The magnitude of the output of phase detector 56 depends on the magnitude of the phase difference between the reference signal and the traversing fraction of the measuring signal, as inputted from buffer amplifier 60 and RF pad 34, respectively. Integrator 62 provides, as an output, a control signal, the magnitude of which is dependent on the magnitude of the signal outputted from phase detector 56, to variable phase shifter 21, and thereby changes the phase angle of the signal outputted from the variable phase shifter 21. With the phase angle of the reference signal thus modified, the combination of the reference signal and the traversing fraction of the measuring signal force the output of the phase detector 56 to a null. The output of the integrator 62, after achieving the null at phase detector 56, is representative of the original phase difference between the output of phase shifter 21, representing the reference signal, and the output of the RF pad 34, representing the traversing fraction of the measuring signal. As shown in FIG. 1, a portion of the output signal from integrator 62 is fed to computer controller 58, as the first representation of the amount of moisture in web 12.

High frequency electric energy source 14 includes a varactor-tuned oscillator 64 and a crystal phase lock 66. A portion of the output of the varactor-tuned oscillator 64 is routed through the crystal phase lock 66, thereby synchronizing the varactor-tuned oscillator 64 with a single-frequency quartz crystal, having a frequency which is a fixed fraction of the frequency of oscillator 64, in the crystal phase lock 66, thereby stabilizing the output of the varactor-tuned oscillator 64.

Reflected power detector 26 comprises a reflected power bridge 68, which receives the reflected fraction of the measuring signal from resonant cavity 50, through switch 30A and bias tee 28, and provides an output to radio frequency detector 70. Radio frequency detector 70 converts the output of the reflected power bridge 68 from a radio frequency (e.g. microwave) signal to a direct current signal, the magnitude of the signal outputted from the radio frequency detector 70 being dependent on the magnitude of the power reflected from the resonant cavity 50.

FIG. 3 shows, in side elevation view, a cross section of a portion of the measuring instrument 10, illustrating the receptacle 32 and appurtenances, in position closely adjacent a web 12 in which moisture and other properties are to be measured. FIG. 3 views web 12 from generally the side of the web, such that the web traverses the instrument 10 from left to right, as shown by arrow 71. In use, the top wall 72 is generally placed in contact with the web 12.

In a preferred instrument 10, both the receptacle 32 and the circuit 1 are designed such that the resonant frequency of the resonant cavity 50 is rather stable. Thus, when the instrument is manufactured, specific materials and structures are used which contribute to consistency of the resonant frequency. Once the manufacture of a given instrument is complete, the instrument is initially calibrated for the resonant frequency of the specific resonant cavity in that specific instrument. With respect to the resonant frequency of the cavity 50, the frequency is specifically related to dimensions of the end walls, side walls, and bottom wall, as well as to the dimensions, placement, and the like of tuned transmission rods 52.

In preferred receptacles 32, the side walls 42, 44, end walls 38, 40, and bottom wall 46, are all constructed of nickel-plated steel. The steel has limited coefficient of thermal expansion. Transmission rods 52 are constructed of a specially selected material which has a very low coefficient of thermal expansion, whereby the contribution of the rods to resonance is generally unaffected by temperature.

For rods 52, the coefficient of thermal expansion is preferably no more than about $4 \times 10^{-6}$ inch per inch length degree Celsius at room temperature. An example of such a material comprises about 60 to about 65 percent by weight iron, about 34 to about 39 percent by weight nickel, and about 0.5 to about 1.5 percent by weight manganese. Such material is available under the Tradename INVAR® as e.g. INVAR 36 from Fry Steel Company, Santa Fe Springs, Calif. INVAR 36 has a chemical analysis of about 62 percent iron, about 36 percent nickel, and about 1 percent manganese, about 0.25 percent selenium, about 0.28 percent silicon, and about 0.08 percent carbon.

Top wall 72 of the instrument serves as an interface between the top surface 48 of the receptacle and the web 12, and thus covers the open top of the receptacle. Top wall 72 is preferably made with material which readily transmits microwave energy, with negligible attenuation, with known fixed amount of change in phase, and with negligible change in frequency. In addition, the top wall should have a low dielectric constant. A dielectric constant of no greater than about 5 is preferred, with a dielectric constant of no greater than about 3 being more preferred. While a variety of polymeric and other such materials can satisfy the above parameters, and thus can be used, preferred materials are acrylonitrile butadiene styrene copolymer, epoxy resin, and polyester fiberglass.

Referring again to FIG. 3, two pairs of optical sensors 74, 76 are disposed on opposing sides of the receptacle 32, adjacent but spaced from the top surface 48, such that the optical sensors 74, 76 are adjacent but spaced from the web 12 when the instrument is being used as shown in FIG. 3. Only one sensor of each pair is shown. As disposed in the instrument 10, and as suggested by FIG. 3, each pair of optical sensors is preferably aligned transverse to the transmission rods 52, and thus is aligned perpendicular to the direction of travel of web 12.

The purpose of the optical sensors 74, 76 is to sense a line 78 or other mark, or marks, e.g. generally extending across the width of the web as the line intermittently passes the optical sensors during normal traverse of the web from left to right as the web is being used on a papermaking machine, and as illustrated in FIG. 3. Line 78 can be a dashed line, or other intermittently structured line. The sensors 74, 76 feed the sensed information to the computer controller 58. Preferably, the instrument 10 is held against the web long enough for at least the sensors 74 to read a such line 78 at least twice as the web is travelling in its closed loop path.

Computer controller 58 uses the amount of time for the line to travel the known distance from the first pair of sensors 74 to the second pair of sensors 76, to compute the speed at which the web is travelling. The computer controller uses the amount of time for a given line 78 to be sensed twice by the same optical sensors (e.g. 74), in combination with the computed web speed, to determine the length of the web.

A temperature sensor 80 is also disposed in adjacent but spaced from the top surface 48 of the receptacle 32, such that the temperature sensor 80 is also adjacent but spaced from the web 12 when the instrument 10 is being used to collect data about the web, as shown in FIG. 3. A preferred temperature sensor senses the temperature of the web without contacting the web. A suitable such temperature sensor is an infrared sensor. An infrared sensors is preferred because infrared sensors measure temperature without contacting the web, and thus the temperature so read is not affected by frictional contact with the (e.g. moving) web.

The temperature so sensed is inputted to computer controller 58. In the embodiments contemplated, the temperature is repeatedly sensed, so as to provide a profile of temperature across the width of the web 12, or along the length of the web, in accord with the relative path traversed by the instrument 10 with respect to the web 12.

The response time of the circuit, namely the time interval between successive output readings of the computer controller 58, as to moisture calculated from output signals from the phase difference detector and the reflected power detector, is limited only by the response time of the phase locked loop in the phase difference detector 36. In preferred embodiments, the repeat rate of the circuit is at least 300 readings per second, preferably at least 500 readings per second. Repeat rates of 1000, 2000, 3000, 4000, and in excess of 5000 readings per second are contemplated as being possible.

In order for the instrument 10 to provide reliable readings as to moisture content of the web 12, the instrument must be calibrated, in order to provide standard references against which readings are taken and results are calculated. The calibration has two phases.

The first phase of the calibration function is performed with the receptacle 32 switched into the circuit. With switches 30A, 30B set in the default settings, the control input to bias tee 28 is first adjusted to give the desired amount of mismatch to varactor diode 54, thereby adjusting the sensitivity of the resonant cavity 50, to moisture, to a convenient scale, as well as affecting the relative amounts of the traversing fraction and the reflected fraction of the signal. Then the control signal to phase shifter 22 is adjusted to bring the output of integrator 62 to a preferred level, e.g.

4.1 volts. Thus is the variable phase shifter 22 employed to correct for circuit deviations or drift, using phase shifter 22 to vary the phase length of the measuring path, and thus to bring the output of the integrator 62 to the preferred level.

Switches 30A, 30B are then set to the alternate settings, whereby the measuring signal passes, from switch 30A to switch 30B, through the calibration line 51 to measure and thereby establish a reference standard e.g. at about 2 volts. The reflected power caused by the impedance mismatch in the calibration line circuit is also read and recorded by computer controller 58. This concludes the initial field calibration of the instrument. The instrument is further calibrated on the fly during routine use, as discussed later herein.

With respect to the phase shifting function of the circuit, calibration line 51 provides a route of known phase delay independent of moisture, whereby the output signal of phase difference detector 36 depends only on phase shifting caused by circuit elements outside resonant cavity 50. Thus is the net phase shift affect of the circuit elements outside the resonant cavity isolated from the phase shift caused by the resonant cavity.

When the circuit is then returned to the use mode by switching the resonant cavity back into the circuit, any deviation of the output of the integrator 62, from the reference (e.g. 4.1) voltage is caused by the cavity 50, and specifically by the moisture in the web 12 as the web passes by the cavity 50.

Still referring to the calibration mode, phase two, of the instrument, the calibration line circuit, from and including switches 30A, 30B, through the calibration line 51, includes a known amount of impedance mismatch. With the signal routed through the coaxial calibration line 51, the known amount of impedance mismatch causes reflection of a portion of the measuring signal back through bias tee 28, through reflected power bridge 68, to the radio frequency detector 70. The amount of reflection received from the known standard amount of impedance mismatch provides a standard against which the amount of reflection from resonant cavity 50 may be measured. The calibration reading is inputted to computer controller 58.

In phase one of calibration, the switches 30A, 30B are aligned as shown in FIG. 1 to pass the measuring signal through the resonant cavity 50. A varying control signal is supplied through bias tee 28 to change the reactive impedance of the variable matching device 54, thereby to set the ratio of the traversing fraction of the measuring signal to the reflected fraction of the measuring signal. The control signal supplied to bias tee 28 is varied until the reflected power measured by the reflected power detector 26 reaches its lowest point, resulting in a reflected power measurement representing a desired value for the circuit 1. The desired value is then inputted to controlling computer 58 and used as a reference for later measurements of reflected power and phase difference.

The calibration function, both phases one and two, is performed in ambient conditions, away from concentrations of moisture, for example, pointed away from a moist web such as a moist felt on a papermaking machine. The calibration mode is preferably entered manually by the operator of the instrument before, and optionally after, using the instrument to collect a moisture reading, in order to assure that the circuit has not drifted away from the calibration point while the readings were being taken.

The control signal input to phase shifter 22 is maintained while the instrument 10 is in use taking moisture readings at the web 12. The control signal to phase shifter 22 thus provides a standard for use in analyzing the phase shift in the traversing fraction as the traversing fraction advances along the measuring path through the resonant cavity, to the phase difference detector. By varying the control input to the phase shifter 22 in calibrating the instrument 10, phase shift due to circuit elements can be set and/or restored to a known calibration condition prior to taking measurements with the instrument 10.

To this point, the teaching has, in general, focused on the process for generating a first reading from the phase difference detector, simultaneously generating a second reading from the reflected power detector, and simultaneously feeding the first and second readings to the computer controller, with the computer controller calculating a resultant moisture data value based on the combination of the first and second readings.

In practice, the instrument 10, including the computer controller, repeatedly computes such resultant moisture data values at a high repeat rate. While a wide range of repeat rates is possible, in a preferred instrument 10, the repeat rate is 512 readings per second.

Still referring to a preferred embodiment, computer controller 58 includes first and second memory devices, not shown, to record data values for each reading, each memory storage device having 512 data-receiving elements. As the instrument reads moisture data values, and the computer controller calculates moisture data points from respective such data values, the first 512 such data points are stored, in the sequence received, and as calculated, as a first set of data points in the first memory device. The second 512 data values are similarly arrived at and stored, as a second set of data points, in the sequence received, and as calculated, in the second memory device. Once the second memory device is full, the 512 sequential pairs of data points in the first and second memory devices are averaged, and are stored in the first memory device, each of the data points then in the first memory device representing two phase shift data values and two reflected power data values, received from the circuit 1, and corresponding two calculated data points, as calculated by computer controller 58.

As additional readings are taken, and passed to computer controller 58, the computer controller averages each successive two such data values to derive data points therefrom, before storing the resulting data points in respective data receiving elements in the second memory device. When the second memory device is again full, each data point in each of the first and second memory devices represents two data values, each data value being computed from the combination of one phase shift input and one reflected power input, from the circuit 1. The 512 sequential pairs of data points in the first and second memory devices are again averaged, and are again stored in the first memory device, each of the data points in the first memory device then representing four phase shift data values and four reflected power values, received from the circuit 1, and corresponding four calculated data points, as calculated by computer controller 58.

As additional readings are taken, and passed to computer controller 58, the computer controller averages successive data values, the number of data values averaged being equal to the number data values represented by the data points then in storage in the first memory storage device, before storing the data values as data points in respective data receiving elements in the second memory device. Each time the second memory device is filled up, the data points in the second memory device are averaged into the first memory device.

When collection of readings stops, the second memory device typically contains less than 512 data points. The data points in the second memory device are then dithered into the first memory device. The resulting 512 data points each represent 1/512th of the length of the path over which readings were taken.

The above method of receiving and storing data points provides a method of receiving an unspecified number of data values, and converting the unspecified number of data values into a pre-determined fixed number of data points, each representing the same number of data values. By recording the starting and ending point on the web for which readings were taken, the path along the web can be divided into 512 fractions of equal length, and each data point in the first memory device can be correlated to a respective one of such fractions. The path may, of course traverse along the length of the web, along the width of the web, or at an angle traversing both length and width.

Papermaking felts typically include a visual reference line 78, e.g. a colored line, extending across the web, which can be sensed by optical sensors 74, 76. In preferred embodiments, computer controller also receives, in addition to moisture signals from phase difference detector 36 and reflected power detector 26, sensory signals, indicating the passage of line 78, from the optical sensors. When the computer controller 58 receives and stores the data points as indicated above, it first creates separate subsets of data points, each subset representing the data values received between successive passes of the line 78 past the optical sensors. Thus, each subset of data points represents e.g. a complete length of the web 12.

Line 78 may take on a range of characters. Thus, it may be intermittent. It may have readability other than optical/visual. The important property is that the line 78 be readable by sensors 74, 76, the respective sensors being sensitive to the readable property of the line 78.

Wherever in this teaching, and in the claims following, reference is made to storing first and second sets of data points in respective first and second memory devices, the inventors contemplate that a selected number of data values may be mathematically altered/modified (e.g. averaged) to arrive at the data points to be stored in the first and/or second memory devices. Combining data points from the first and second memory devices into the first memory device and subsequent gathering and storing of data, is then done with consideration for such alterations/modifications.

Periodically, and especially between calculations which alter or modify data points and correspondingly move data points from the first and second memory devices into the first memory device, the instrument 10 automatically makes on-the-fly calibrations, switching in the calibration line 51 for a brief period, to check and correct for any drift that may have occurred in circuit 1 since the previous calibration. Such on-the-fly correction is facilitated by using high speed switching diodes in high speed electronic switches 30A, 30B. High speed switching diodes effectively isolate the moisture affect on the cavity from the calibration line signal during the on-the-fly calibrations.

Simultaneously with the taking of moisture readings as discussed above, the temperature of the web is sensed using infrared detector 80, and the temperature readings are inputted to computer controller 58. The computer controller then adjusts the data values for temperature, using known relationships, before storing the data values in the memory devices as data points.

Vibration sensors, not shown, can be installed at strategic locations on web handling equipment used to convey or operate on the web 12, thus to sense vibration of the web handling equipment. The vibration readings can then be fed into the computer controller 58 simultaneously with the rest of the data discussed above, thus enabling the computer controller to correlate vibration data to specific locations on the web in the same manner as moisture and temperature data are correlated to specific locations on the web.

Given the combined readings regarding moisture content, temperature, and vibration, correlated to specific loci on the web, one can then identify anomalous readings on the web, such as locations where the web is weak, or is wearing more rapidly than anticipated. Given the identity of such anomalous loci, the manufacturing and supply records related to manufacture of that specific web can then be reviewed to correlate, where appropriate, the anomalous data to specific raw material supplies or to manufacturing practices.

It is contemplated that the operation and functions of the invention have become fully apparent from the foregoing description of elements, but for completeness of disclosure the usage of the invention will be briefly described.

With the instrument 10 turned on and warmed up, and away from the web, the input to the bias tee 28 is first adjusted to give the desired amount of mismatch to varactor diode 54, thereby adjusting the sensitivity of the resonant cavity 50, to moisture, to a convenient scale, as well as affecting the relative amounts of the traversing fraction and the reflected fraction of the signal. Then the input to phase shifter 22 is adjusted until the output of the integrator is 4.1 volts.

The switches 30A, 30B are then switched to the alternate position, and the constant frequency signal from power divider 16 is passed through the calibration line to establish a calibration standard at about 2 volts. With switches 30A, 30B in the alternate position, the reflected power caused by the impedance mismatch in the calibration line circuit is also read and recorded by computer controller 58. This concludes the initial field calibration of the instrument. The instrument is then ready to read the moisture in the web 12.

Next, the instrument 10 is placed against a surface of the web 12, bringing the resonant cavity 50 propinquant the web, and respectively the moisture in the web. At that point, the cavity 50 is separated from the web and its moisture only by the top wall 72. With the instrument so positioned against the web, readings are taken and stored as discussed above. The readings include moisture readings, optical readings with respect to reference line 78, vibration in the web handling equipment, and temperature readings. The moisture readings and the temperature readings are stored separately, and are both correlated to passings of the reference line 78 past optical sensors 74, 76. Accordingly, computer controller 58 compensates each moisture reading for the temperature sensed at the infrared detector 80. Also, the computer controller can correlate each moisture reading to the temperature of the web at the locus where the respective reading was taken.

Thus can a series of readings be used to simultaneously determine moisture content of the web, temperature of the web, vibration related to the web, length of the web, and web speed. Given length of the web, the computer controller 58 can correlate specific moisture and the like data values to specific respective segments of the web along the path where readings were taken, as a given fraction of the length of the web, whereby each such data point correlates with a specific segment of the web.

The phase shift occurring in cavity 50 is caused by the dielectric of the water, which is significantly greater than the phase shift caused by ionics or other impurities typically encountered in the water used on a papermaking felt in a papermaking machine, as well as being significantly greater than phase shift caused by materials typically carried in or on the web, such as a plastic substrate, wool, or other fiber batting, and e.g. cellulose in the paper being formed on the web.

The frequency of the signal generated at oscillator 64 is preferably in the range known as microwave frequency, in order to take advantage of the sensitivity of microwave frequency signals to dielectric of any material into which the signal passes. Since the response of the circuit depends on dielectric, instruments of the invention can be used to sense/measure any property which varies in intensity with the dielectric of the material of interest.

The instrument, as illustrated, records 512 moisture readings per second. While temperature is preferably simultaneously recorded, the maximum repeat rate on the temperature reading is controlled by the maximum repeat rate of the temperature sensor, which may be less than the repeat rate for circuit 1. Thus, for a given data point, the respective temperature reading may lag the repeat rate for the moisture reading.

As referred to herein, "dithering" and the like generally comprehends converting a higher number of data points to a lower number of data points, providing resultant data points at a lower resolution, amounting to a form of data compression. Thus, where the number of data points in the second memory device is the same as the number of data points in the first memory device, dithering comprehends treating the combination of the data points in the first and second memory devices as a unit, averaging pairs of successive data points in both the first and second memory devices, and combining the resultant averaged data points so calculated, part from the first memory device, part from the second memory device, into the first memory device, all while maintaining the sequence in which the data values were collected.

Where the number of data points in the second memory device is less than the number of data points in the first memory device, the data points in both of the first and second memory devices are treated as a unit, compressed to 512 data points, reflecting the number of data storage elements in the first memory device, and stored in the first memory device. The actual mechanism for compressing the data points can vary. In one compression embodiment, each of the resultant e.g. 512 data points represents an average of a fractional number of successive data points, or fractions of data points, corresponding to the compression ratio. In this embodiment, each one of the resultant 512 data points represents a common fraction of the length of the path over which the data values were collected.

In a second compression embodiment, the number of data points, in the second memory device, which must be averaged into the first memory device, is first determined. Then that number of averages of successive data points are calculated, evenly spread over the combined set of data points of the first and second memory devices, to arrive at the compressed resultant set of 512 data points, and the resultant 512 data points are stored in the first memory device. In this embodiment, some of the resultant data points in the first memory device represent more data values than other resultant data points. Thus, each data point represents one of first and second different fractions of the length of the path over which the data values were collected. Where there are 512 resultant data points, the first fraction is greater than $1/512$, and the second fraction is less than $1/512$.

The fixed number of data elements in the respective memory devices can be based on hardware limitations, software-imposed limitations, or a combination of hardware and software limitations.

As contemplated herein, computer controller 58 is a digital control module integral in instrument 10, which is a portable, hand-held device weighing less than e.g. 10 pounds, preferably less than 5 pounds.

As referred to herein, "data values" generally relate to values received from circuit 1 prior to mathematical manipulation by computer controller 58, whereas "data Points" generally relate to such values after mathematical manipulation by the computer controller, e.g. to compensate for temperature or other non-moisture variable, or to dither information from the first and second memory devices into the first memory device.

The first and second memory devices are discussed above with respect to storing moisture data. Corresponding additional first and second memory devices can, and preferably are, used to store temperature, vibration, speed, length, and like data, in like manner, for use in the several calculations.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

Having thus described the invention, what is claimed is:

1. A measuring system for measuring the amount of dielectric in a web, said measuring system including a measuring instrument having an electric circuit, including a plurality of circuit elements, said electric circuit comprising:
    (a) an electric energy source, for emitting a constant frequency signal;
    (b) a power divider for dividing the constant frequency signal into a reference signal at a reference terminal, for travelling along a reference path, and a measuring signal at a measuring terminal, for travelling along a measurement path;
    (c) a receptacle comprising a resonant cavity having at least one resonant frequency, said receptacle being electrically connected to said electric energy source such that a first traversing fraction of the measuring signal, corresponding to the at least one resonant frequency, traverses along the measurement path, through said resonant cavity, and wherein a second fraction of the measuring signal is reflected from said resonant cavity, said receptacle being positioned in said measuring instrument to accommodate placing said resonant cavity proximate the web, said resonant cavity being adapted to cause a phase shift in the traversing fraction in response to the dielectric in the web, such that the phase of the traversing fraction of the measuring signal is shifted relative to the phase of the reference signal, the magnitude of the phase shift in the traversing fraction of the measuring signal being a function of the amount of dielectric in the web;
    (d) a phase difference detector for receiving the reference signal and the traversing fraction of the measuring signal after the traversing fraction traverses said resonant cavity, said phase difference detector being adapted to detect the difference between the phase of the reference signal and the phase of the traversing fraction of the measuring signal and to provide a first output signal, the magnitude of the first output signal depending on the magnitude of the difference in phase so detected, the first output signal providing a first representation of the amount of dielectric in the web; and
    (e) a reflected power detector electrically connected in the electric circuit between said receptacle, and with said measuring terminal of said power divider, for providing a second output signal, the magnitude of the second output signal depending on the magnitude of the reflected second fraction of the measuring signal, the second output signal thus comprising a second representation of the amount of dielectric in the web.

2. A measuring system as in claim 1, including a controller adapted to compare the first and second output signals to data stored in said controller, thereby to cancel out the affect of the distance between said resonant cavity and the dielectric being detected, and to generate a third output signal, the third output signal being a more nearly accurate representation of the dielectric in the web than either of the first and second output signals.

3. A measuring system as in claim 1 wherein the difference in phase, as detected in said phase difference detector, is a function of dielectric properties extant in the web.

4. A measuring system as in claim 1 wherein said electric energy source comprises, in combination, a varactor-tuned oscillator having a third output signal, a single-frequency crystal oscillator having a fourth output signal, and a phase-locking circuit comprising said varactor-tuned oscillator and said single-frequency crystal oscillator, a portion of said third output signal being routed through said phase locking circuit, said phase locking circuit being configured to synchronize said varactor tuned oscillator with said single-frequency crystal oscillator to thereby stabilize the frequency of the third output signal.

5. A measuring system as in claim 1 wherein said receptacle comprises a tuned transmission line in said resonant cavity and a variable matching device for altering the reactive impedance of said resonant cavity.

6. A measuring system as in claim 5 wherein said tuned transmission line comprises first and second transmission rods.

7. A measuring system as in claim 6, said transmission line having input and output terminals, said variable matching device comprising a varactor diode electrically connected to at least one of said first and second transmission rods.

8. A measuring system as in claim 1, said receptacle having a plurality of walls, and an open top, including a top surface, said measuring instrument comprising a top wall propinquant said top surface, said top wall being adapted to transmit microwave energy from said resonant cavity with negligible attenuation, a fixed amount of change in phase, and negligible change in frequency, a transmission line in said receptacle, said transmission line being constructed of material having a coefficient of thermal expansion no greater than $4 \times 10^{-6}$ inch per inch length degree Celsius at room temperature.

9. A measuring system as in claim 8, said transmission line being constructed of material comprising about 60 to about 65 percent by weight iron, about 34 to about 39 percent by weight nickel, and about 0.5 to about 1.5 percent by weight manganese.

10. A measuring system as in claim 8, said top wall comprising material having a dielectric constant no greater than about 5.

11. A measuring system as in claim 8, said top wall comprising material having a dielectric constant no greater than about 3.

12. A measuring system as in claim 1 wherein said phase difference detector comprises a phase locked loop, including a variable phase shifter having a third output signal; a phase detector having a fourth output signal, and having as input signals, the third output signal of said phase shifter, and the first traversing fraction of the measuring signal as modified by passage through said resonant cavity; and an integrator having, as an input signal, the fourth output signal of said phase detector, said integrator providing a fifth output signal, including a control signal to said variable phase shifter for forcing the reference signal and the first traversing fraction of the measuring signal to arrive at said phase detector in quadrature, and thereby forcing the output signal of said phase detector to a null, the output signal of said integrator after achieving the null being representative of the phase difference between the reference signal and the first traversing fraction of the measuring signal.

13. A measuring system as in claim 5, said electric circuit including a bias tee electrically connected between said measuring terminal of said power divider and said resonant cavity, for providing a bias on said variable matching device, to thereby control the sensitivity, of said tuned transmission line, to the amount of dielectric in the web.

14. A measuring system as in claim 1, said electric circuit including a variable phase shifter connected in series with said measuring terminal of said power divider, and a variable control input signal to said variable phase shifter, for varying the phase length of the measurement path, thereby to compensate for circuit errors and to establish a known calibration condition for taking measurements.

15. A measuring system as in claim 1, said electric circuit including first and second switching devices electrically connected to the input and output terminals, respectively, of said resonant cavity, a first position of said switching devices directing the measuring signal to said resonant cavity, a second position of said switching devices directing the measuring signal to bypass said resonant cavity and pass along an alternate signal path, the alternate signal path providing a phase shift standard, independent of dielectric adjacent the resonant cavity, whereby the first output signal of said phase difference detector correlates with phase shift caused by circuit elements within said measuring instrument.

16. A measuring system as in claim 15 wherein the alternate signal path comprises a signal conductor of known phase length.

17. A measuring system as in claim 15, said electric circuit including a variable phase shifter, having a variable control input signal, for varying the phase length of the measurement path, connected in series with said measuring terminal of said power divider, and wherein, when said first and second switching devices are positioned to bypass said resonant cavity, said phase shifter control input signal can be varied to change the phase length of the measurement path, thereby compensating for circuit errors and restoring a known calibration condition prior to taking measurements.

18. A measuring system as in claim 1, including a temperature measuring device, for measuring temperature in the web, and means to compensate the first output signal for temperature variations.

19. A measuring system as in claim 2, including a temperature measuring device, for measuring temperature in the web, and means to compensate the first output signal for temperature variations.

20. A measuring system as in claim 18 wherein said temperature measuring device comprises an infrared detector.

21. A measuring system as in claim 19 wherein said temperature measuring device comprises an infrared detector.

22. A measuring system as in claim 1, said electric circuit including at least one attenuation device and at least one signal amplification device in series with each of the measurement path and the reference path, said at least one attenuation device in each said path being effective to attenuate power reflected back through the respective circuit elements toward said power divider, said at least one signal amplification device in each said path being effective to maintain amplitudes in the respective signals sufficient for detecting the phase difference between the reference signal and the traversing fraction of the measuring signal in said phase difference detector.

23. A measuring system as in claim 1 wherein said reflected power detector comprises a reflected power bridge and a radio frequency detector.

24. A measuring system as in claim 1 wherein said reflected power detector comprises a reflected power bridge having a third output signal, and a radio frequency detector electrically connected to said reflected power bridge, to measure the magnitude of the third output signal, and to provide a fourth output signal dependent on the magnitude of the third output signal.

25. A measuring system as is claim 1, including a calibration line of known phase length, and a switch for periodically and temporarily switching said receptacle out of the electric circuit and respectively switching said calibration line into the electric circuit, thereby to periodically recalibrate the electric circuit based on the known phase length of said calibration line.

26. A measuring system as in claim 25, including a bias device between said switch and said measuring terminal of said power divider, thereby to adjust sensitivity of said resonant cavity.

27. A measuring system as in claim 25, including a phase shifter between said switch and said measuring terminal of said power divider, thereby to adjust said output signal to a desired output when said measuring instrument is away from concentrations of dielectric.

* * * * *

UNITED STATES PATENT AND TRADEMARK OFFICE
CERTIFICATE OF CORRECTION

PATENT NO. : 5,838,158
DATED : November 17, 1998
INVENTOR(S) : David A. Beck et al.

It is certified that error appears in the above-identified patent and that said Letters Patent is hereby corrected as shown below:

On the cover page, item [57] Abstract, line 17, change "affect" to --effect--.

In the Specification:
Column 19, line 11, change ""data Points"" to --"data points"--.

Signed and Sealed this

Twenty-seventh Day of February, 2001

Attest:

NICHOLAS P. GODICI

Attesting Officer    Acting Director of the United States Patent and Trademark Office